(12) United States Patent
Mikami et al.

(10) Patent No.: US 8,809,557 B2
(45) Date of Patent: Aug. 19, 2014

(54) METHOD FOR PRODUCING OPTICALLY ACTIVE FLUORINATED OXETANE

(75) Inventors: Koichi Mikami, Tokyo (JP); Kohsuke Aikawa, Tokyo (JP); Junpei Aida, Tokyo (JP); Akihiro Ishii, Kawagoe (JP); Misugi Kato, Kawagoe (JP); Takashi Masuda, Kawagoe (JP)

(73) Assignees: Central Glass Company, Limited, Ube-shi (JP); Tokyo Institute of Technology, Tokyo (JP)

( * ) Notice: Subject to any disclaimer, the term of this patent is extended or adjusted under 35 U.S.C. 154(b) by 295 days.

(21) Appl. No.: 13/201,171

(22) PCT Filed: Feb. 22, 2010

(86) PCT No.: PCT/JP2010/052638
§ 371 (c)(1),
(2), (4) Date: Aug. 11, 2011

(87) PCT Pub. No.: WO2010/098288
PCT Pub. Date: Sep. 2, 2010

(65) Prior Publication Data
US 2011/0306781 A1 Dec. 15, 2011

(30) Foreign Application Priority Data

Feb. 26, 2009 (JP) .............................. 2009-044684
Feb. 19, 2010 (JP) .............................. 2010-034169

(51) Int. Cl.
*C07D 305/04* (2006.01)

(52) U.S. Cl.
CPC .................................... *C07D 305/04* (2013.01)
USPC ....................................................... 549/510

(58) Field of Classification Search
CPC .................................................... C07D 305/04
USPC ....................................................... 549/510
See application file for complete search history.

(56) References Cited

PUBLICATIONS

Zhurnal Organicheskoi Khimii (Russia), 1989, vol. 25, pp. 2523-2527.
Viacheslav A. Petrov et al., "Quadricyclane—thermal cycloaddition to polyfluorinated carbonyl compounds A simple synthesis of polyfluorinate 3-oxatricyclo[4.2.1.02,5]non-7-enes", Journal of Fluorine Chemistry (Netherlands), 2004, vol. 125, pp. 1543-1552.
Marco Molteni et al., "Fluorinated peptidomimetics: synthesis, conformational and biological features", Journal of Fluorine Chemistry (Netherlands), 2004, vol. 125, pp. 1735-1743.
Theodora W. Greene et al., "Protective Groups in Organic Synthesis", Third Edition, 1999, John Wiley & Sons, Inc.
"Catalytic Asymmetric Synthesis", Second Edition, 2000, pp. 34-83, Wiley-VCH, Inc.
Kohsuke Aikawa et al., "Asymmetric catalysis of ene reactions with trifluoropyruvate catalyzed by dicationic palladium(II) complexes", Tetrahedron Letters (U.K.), 2004, vol. 45, pp. 183-185.
Koichi Mikami et al., "Enantioselective catalysis of carbonyl-ene and Friedel-Crafts reactions with trifluoropyruvate by 'naked' palladium(II) complexes with SEGPHOS ligands", Tetrahedron: Asymmetry (U.K.), 2004, vol. 15, pp. 3885-3889.
Koichi Mikami et al., "Enantiodiscrimination and Enantiocontrol of Neutral and Cationic $Pt^{II}$ Complexes Bearing the *Tropos* Biphep Ligand: Application to Asymmetric Lewis Acid Catalysis", Angew. Chem. Int. Ed. (Germany), 2005, vol. 44, pp. 7257-7260.
Simon Doherty et al., "Asymmetric Platinum Group Metal-Catalyzed Carbonyl-Ene Reactions: Carbon—Carbon Bond Formation versus Isomerization", J. Org. Chem. (U.S.), 2006, vol. 71, pp. 9751-9764.
David A. Evans et al., "$C_2$-Symmetric Copper(II) Complexes as Chiral Lewis Acids, Scope and Mechanism of the Catalytic Enantioselective Aldol Additions of Enolsilanes to Pyruvate Esters", J. Am. Chem. Soc. (U.S.), 1999, vol. 121, pp. 686-699.
Koichi Mikami et al., "Asymmetric synthesis by enantiomer-selective activation of racemic catalysts", Nature (U.K.), Feb. 1997, vol. 385, pp. 613-615.
Takahiko Akiyama et al., "Stereoselective Construction of Oxetane by Titanium (IV) Chloride Promoted [2+2] Cycloaddition of allylsilanes to α-Keto Esters", Chemistry Letters, 1995, No. 8, pp. 723-724.
I.L. Knunyants et al., "Reactions of Alkyl-trifluoropyruvates with Nucleophilic Reagents", Chemical Abstracts, 1968, vol. 69, pp. 6285.
P. Mueller et al., "Rh (II)-Catalyzed Asymmetric Carbene Transfer with Ethyl 3,3,3-Trifluoro-2-diazopropionate" Tetrahedron, 2004, vol. 60, No. 22, pp. 4755-4763.
Junpei Aida et al., "Fusei Lewis San Sokubai o Mochiita Shinki Kanka Fuka Hanno no Kaihatsu (Development of Novel Cycloaddition Reaction Using Asymmetric Lewis Acid Catalyst)" Proceedings of the Chemical Society of Japan, Mar. 13, 2009, vol. 89, No. 2, pp. 1029.
International Search Report including English language translation dated Mar. 16, 2010 (Five (5) pages).
PCT/ISA/237 Form (Three (3) pages), Mar. 16, 2010.

*Primary Examiner* — Andrew D Kosar
*Assistant Examiner* — Raymond Covington
(74) *Attorney, Agent, or Firm* — Crowell & Moring LLP

(57) ABSTRACT

Disclosed is a method of producing an optically active fluorinated oxetane, which can be an important pharmaceutical or agricultural intermediate, by reaction of a fluorinated α-keto ester with an acyl alkenyl ether in the presence of a transition metal complex with an optically active ligand. This method utilizes a catalytic asymmetric synthesis process and does not require a stoichiometric amount of chiral source. It is thus possible to dramatically reduce the amount of use of the asymmetric catalyst especially when the reaction is performed at a high concentration of substrate (with the use of a small amount of reaction solvent) or in the absence of a reaction solvent (under neat conditions). Further, the target optically active fluorinated oxetane can be obtained with high yield and with very high optical purity. The product contains almost no difficult-to-separate impurity and shows high chemical purity.

5 Claims, No Drawings

METHOD FOR PRODUCING OPTICALLY ACTIVE FLUORINATED OXETANE

TECHNICAL FIELD

The present invention relates to a method for producing an optically active fluorinated oxetane, which can be an important pharmaceutical or agricultural intermediate.

BACKGROUND ART

An optically active fluorinated oxetane of interest of the present invention is a novel compound that can be an important pharmaceutical or agricultural intermediate. There has however been reported no methods for production of the optically active fluorinated oxetane. As shown in Scheme 1, it is assumed that the optically active fluorinated oxetane is a synthetic equivalent having on an asymmetric carbon atom thereof a trifluoromethyl group and a hydroxyl group and can be derived into a desired α,α-disubstituted optically active β,β,β-trifluoroethanol by selective conversion of formylmetyl and alkoxycarbonyl functional groups of different oxidation levels.

Scheme 1

[Chem. 1]

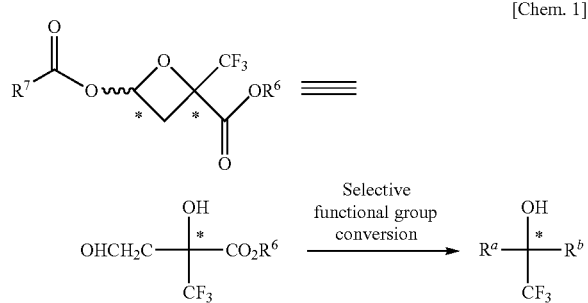

Suitable example of optically active fluorinated oxetane
$R^a$, $R^b$: desired substituent groups Non-Patent Publications 1 to 3 report production methods of compounds structurally different from, but relevant to, the optically active fluorinated oxetane of interest of the present invention.

PRIOR ART DOCUMENTS

Non-Patent Documents

Non-Patent Document 1:
Zhurnal Organicheskoi Khimii (Russia), 1989, Vol. 25, P. 2523-2527
Non-Patent Document 2:
Journal of Fluorine Chemistry (Netherlands), 2004, Vol. 125, P. 1543-1552
Non-Patent Document 3:
Journal of Fluorine Chemistry (Netherlands), 2004, Vol. 125, P. 1735-1743

SUMMARY OF THE INVENTION

It is an object of the present invention to provide a method for producing an optically active fluorinated oxetane, which can be an important pharmaceutical or agricultural intermediate. Each of the production methods of Non-Patent Publications 1 and 2 is intended for production of the relevant compound as a racemic modification and thus cannot be adopted for production of the target optically active compound of the present invention. Further, the production method of Non-Patent Publication 3 is intended for production of the optically active compound but requires a plurality of process steps with the use of a stoichiometric amount of chiral auxiliary.

There has thus been a strong demand to develop a practical production method of a novel optically active fluorinated oxetane compound that can be an important pharmaceutical or agricultural intermediate.

Means for Solving the Problems

The present inventors have found, as a result of extensive researches made to solve the above problems, that it is possible to produce an optically active fluorinated oxetane of the general formula [3] by reaction of a fluorinated α-keto ester of the general formula [1] with an acyl alkenyl ether of the general formula [2] in the presence of "a transition metal complex with an optically active ligand".

The fluorinated α-keto ester of the general formula [1] is preferably one having a trifluoromethyl group as a perfluoroalkyl group and a methyl group or an ethyl group as an alkyl group of its ester moiety so that the fluorinated α-keto ester can be easily available on a large scale. The acyl alkenyl ether of the general formula [2] is preferably one having a hydrogen atom or an alkyl group as a substituent of its acyl moiety and hydrogen atoms as all of three substituents of its alkenyl moiety so that the acyl alkenyl ether can be easily available on a large scale and at low cost. Further, the transition metal complex with the optically active ligand is preferably a divalent cationic transition metal complex with an optically active ligand, more preferably a divalent cationic palladium complex with an optically active ligand. The desired reaction can proceed favorably by the use of such a complex.

The optically active fluorinated oxetane of the general formula [3] obtained by the production method of the present invention is a novel compound that can be an important pharmaceutical or agricultural intermediate. Among others, preferred examples of the optically active fluorinated oxetane are those in which: the perfluoroalkyl group is a trifluoromethyl group; the alkyl moiety of the ester moiety is a methyl group or an ethyl group; the substituent of the acyl moiety is a hydrogen atom or an alkyl group; and all of the other three substituents on the oxetane ring are hydrogen atoms. These oxetane compounds can be produced on a large scale and can be a particularly important pharmaceutical or agricultural intermediate.

As mentioned above, the present inventors have found useful techniques for production of the novel optically active fluorinated oxetane compound. The present invention is made based on such findings.

Namely, the present invention provides a practical production method of an optically active fluorinated oxetane, which can be an important pharmaceutical or agricultural intermediate, as defined in the following Inventive Aspects 1 to 5.

[Inventive Aspect 1]

A method for producing an optically active fluorinated oxetane of the general formula [3], comprising: reacting a fluorinated α-keto ester of the general formula [1] with an acyl alkenyl ether of the general formula [2] in the presence of a transition metal complex with an optically active ligand,

[Chem. 2]

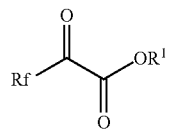

[1]

where Rf represents a perfluoroalkyl group; and $R^1$ represents an alkyl group;

[Chem. 3]

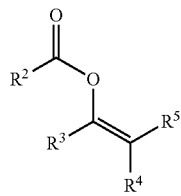

[2]

where $R^2$, $R^3$, $R^4$ and $R^5$ each independently represent a hydrogen atom, an alkyl group, a substituted alkyl group, an aromatic ring group or a substituted aromatic ring group; and

[Chem. 4]

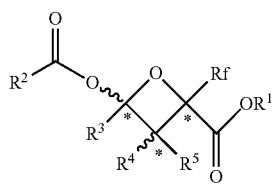

[3]

where Rf, $R^1$, $R^2$, $R^3$, $R^4$ and $R^5$ are the same as above: * represents an asymmetric carbon atom (when $R^4$ and $R^5$ are the same substituents, a carbon atom to which $R^4$ and $R^5$ are bonded is not an asymmetric carbon atom); and the wavy lines indicate that the configuration of acyloxy ($R^2CO_2$) group relative to Rf and the configuration of $R^4$ relative to Rf are each independently a syn configuration, an anti configuration or a mixture thereof.

[Inventive Aspect 2]

A method for producing an optically active fluorinated oxetane of the general formula [6], comprising: reacting a fluorinated α-keto ester of the general formula [4] with an acyl alkenyl ether of the general formula [5] in the presence of a divalent cationic transition metal complex with an optically active ligand,

[Chem.5]

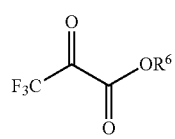

[4]

where $R^6$ represents a methyl group or an ethyl group;

[Chem. 6]

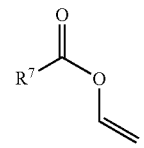

[5]

where $R^7$ represents a hydrogen atom or an alkyl group; and

[Chem. 7]

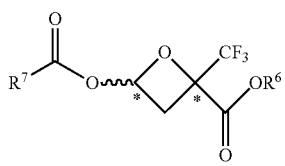

[6]

where $R^6$ and $R^7$ are the same as above; * represents an asymmetric carbon atom; and the wavy line indicates that the configuration of acyloxy ($R^7CO_2$) group relative to $CF_3$ group is a syn configuration, an anti configuration or a mixture thereof.

[Inventive Aspect 3]

The method for producing the optically active fluorinated oxetane according to Inventive Aspect 2, wherein the divalent cationic transition metal complex with the optically active ligand is a divalent cationic palladium complex with an optically active ligand.

[Inventive Aspect 4]

An optically active fluorinated oxetane of the general formula [3]

[Chem. 8]

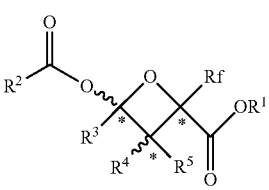

[3]

where Rf represents a perfluoroalkyl group; $R^1$ represents an alkyl group; $R^2$, $R^3$, $R^4$ and $R^5$ each independently represent a hydrogen atom, an alkyl group, a substituted alkyl group, an aromatic ring group or a substituted aromatic ring group; * represents an asymmetric carbon atom (when $R^4$ and $R^5$ are the same substituents, a carbon atom to which $R^4$ and $R^5$ are bonded is not an asymmetric carbon atom); and the wavy lines indicate that the configuration of acyloxy ($R^2CO_2$) group relative to Rf and the configuration of $R^4$ relative to Rf are each independently a syn configuration, an anti configuration or a mixture thereof.

[Inventive Aspect 5]

An optically active fluorinated oxetane of the general formula [6]

[Chem. 9]

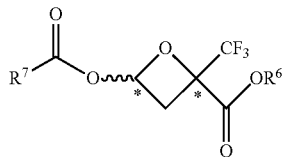

[6]

where $R^6$ represents a methyl group or an ethyl group; $R^7$ represents a hydrogen atom or an alkyl group; * represents an asymmetric carbon atom; and the wavy line indicates that the configuration of acyloxy ($R^7CO_2$) group relative to $CF_3$ group is a syn configuration, an anti configuration or a mixture thereof.

DETAILED DESCRIPTION

The production method of the present invention utilizes a catalytic asymmetric synthesis process and does not require a stoichiometric amount of chiral source so that it is possible to dramatically reduce the amount of asymmetric catalyst used especially when the reaction is performed at a high concentration of substrate (with the use of a small amount of reaction solvent) or in the absence of a reaction solvent (under neat conditions). Further, the target optically active fluorinated oxetane can be obtained with high yield and with very high optical purity. The product contains almost no difficult-to-separate impurity and shows high chemical purity. The usability of the production method of the present invention is thus clear.

In this way, the present invention enables practical production of the optically active fluorinated oxetane that can be an important pharmaceutical or agricultural intermediate.

The production method of the optically active fluorinated oxetane according to the present invention will be described in detail below.

In the fluorinated α-keto ester of the general formula [1], Rf represents a perfluoroalkyl group. Examples of the perfluoroalkyl group as Rf are those of 1 to 12 carbon atoms. The perfluoroalkyl group, when having 3 or more carbon atoms, can be in the form of a linear, branched or cyclic structure. In the fluorinated α-keto ester of the general formula [1], $R^1$ represents an alkyl group. Examples of the alkyl group as $R^1$ are those of 1 to 12 carbon atoms. The alkyl group, when having 3 or more carbon atoms, can be in the form of a linear, branched or cyclic structure. Among others, it is preferable to use a fluorinated α-keto ester having a trifluoromethyl group as Rf and a methyl or ethyl group as $R^1$, which can be easily produced and industrially applicable, for production of the optically active fluorinated oxetane.

It suffices to use the fluorinated α-keto ester of the general formula [1] in an amount of 0.2 mol or more per 1 mol of the acyl alkenyl ether of the general formula [2]. The amount of the fluorinated α-keto ester of the general formula [1] used is preferably 0.3 to 7 mol, more preferably 0.4 to 5 mol, per 1 mol of the acyl alkenyl ether of the general formula [2], In the acyl alkenyl ether of the general formula [2], $R^2$, $R^3$, $R^4$ and $R^5$ each independently represent a hydrogen atom, an alkyl group, a substituted alkyl group, an aromatic ring group or a substituted aromatic ring group. Examples of the alkyl group as $R^2$, $R^3$, $R^4$, $R^5$ are those of 1 to 12 carbon atoms. The alkyl group, when having 3 or more carbon atoms, can be in the form of a linear, branched or cyclic structure. Examples of the aromatic ring group are those of 1 to 18 carbon atoms, including an aromatic hydrocarbon groups, such as phenyl, naphthyl or anthryl and an aromatic heterocyclic group containing a heteroatom e.g. nitrogen, oxygen or sulfur, such as pyrrolyl, furyl, thienyl, indolyl, benzofuryl or benzothienyl.

Examples of the substituted alkyl group and the substituted aromatic ring group are those in which any of the carbon atoms of the alkyl group and the aromatic ring group are replaced with any number of and any combination of substituents. As such substituents, there can be used: halogen atoms such as fluorine, chlorine, bromine and iodine; azide group; nitro group; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; lower alkylamino groups such as dimethylamino, diethylamino and dipropylamino; lower alkylthio groups such as methylthio, ethylthio and propylthio; cyano group; lower alkoxycarbonyl groups such as methoxycarbonyl, ethoxycarbonyl and propoxycarbonyl; aminocarbonyl group; lower alkylaminocarbonyl groups such as dimethylaminocarbonyl, diethylaminocarbonyl and dipropylaminocarbonyl; unsaturated groups such as lower alkenyl groups and lower alkynyl groups; aromatic ring groups such as phenyl, naphthyl, pyrrolyl, furyl and thienyl; aromatic ring oxy groups such as phenoxy, naphthoxy, pyrrolyloxy, furyloxy and thienyloxy; aliphatic heterocyclic groups such as piperidyl, piperidino and morpholinyl; hydroxyl group; protected hydroxyl groups; amino groups (including amino acids or peptide residues); protected amino groups; thiol group; protected thiol groups; aldehyde group; protected aldehyde groups; carboxyl group; and protected carboxyl groups.

In the present specification, the following terms are herein defined by the following meanings. The term "lower" means that the group to which the term is attached has 1 to 6 carbon atoms in the form of a linear structure, a branched structure or a cyclic structure (in the case of 3 or more carbon atoms). It means that, when the "unsaturated group" is a double bond (alkenyl group), the double bond can be in either or both of E and Z geometries. The "protected hydroxyl, amino, thiol, aldehyde and carboxyl groups" may refer to those having protecting groups as described in "Protective Groups in Organic Synthesis", Third Edition, 1999, John Wiley & Sons, Inc. (In this case, two or more functional groups may be protected with one protecting group.)

Further, the "unsaturated group", "aromatic ring group", "aromatic ring oxy group" and "aliphatic heterocyclic group" may be substituted with halogen atoms, azide group, nitro group, lower alkyl groups, lower haloalkyl groups, lower alkoxy groups, lower haloalkoxy groups, lower alkylamino groups, lower alkylthio groups, cyano group, lower alkoxycarbonyl groups, aminocarbonyl group, lower alkylaminocarbonyl groups, hydroxyl group, protected hydroxyl groups, amino group, protected amino groups, thiol group, protected thiol groups, aldehyde group, protected aldehyde groups, carboxyl group or protected carboxyl groups. Although some of these substituent groups may be involved in a side reaction, the desired reaction can be promoted favorably by the adoption of suitable reaction conditions. Among others, it is preferable to use an acyl alkenyl ether having a hydrogen atom or alkyl group as $R^2$ and hydrogen atoms as all of $R^3$, $R^4$ and $R^5$, which can be produced at low cost and industrially applicable, for production of the optically active fluorinated oxetane. In some case, it may be possible to obtain a favorable result by subjecting the acyl alkenyl ether to distillation purification before the reaction.

Although an alkyl alkenyl ether and a silyl alkenyl ether are similar to the acyl alkenyl ether, each of the alkyl alkenyl ether and the silyl alkenyl ether is unstable toward Lewis acids and readily polymerized. It is thus necessary to use an asymmetric catalyst of weak Lewis acidity (impossible to use an asymmetric catalyst of strong Lewis acidity) in combination with the alkyl alkenyl ether or silyl alkenyl ether so that the amount of the asymmetric catalyst used cannot be reduced dramatically. In the case of the alkyl alkenyl ether, a desired oxetane structure cannot be formed during the reaction. In the case of the silyl alkenyl ether, it is necessary for the formation of an oxetane structure to use a silyl alkenyl ether having a sterically bulky silyl group, such as triisopropyl silyl alkenyl ether, that is expensive as the raw material substrate.

Examples of the transition metal complex with the optically active ligand are divalent cationic transition metal catalysts with optically active ligands as represented by the general formula [7]

[Chem. 10]

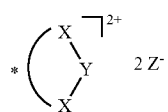

[7]

where X—*—X represents an optically active SEGPHOS derivative (FIG. A), an optically active BINAP derivative (FIG. B), an optically active BIPHEP derivative (FIG. C), an optically active P-Phos derivative (FIG. D), an optically active PhanePhos derivative (FIG. E), an optically active 1,4-Et$_2$-cyclo-C$_6$H$_8$-NUPHOS (FIG. F) or an optically active BOX derivative (FIG. G); Y represents Ni, Pd, Pt or Cu; and Z represents SbF$_6$, ClO$_4$, BF$_4$, OTf (Tf: CF$_3$SO$_2$), AsF$_6$, PF$_6$ or B(3,5-(CF$_3$)$_2$C$_6$H$_3$)$_4$.

[Chem. 11]

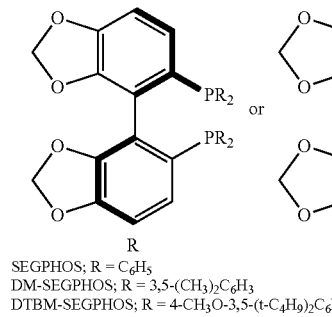

SEGPHOS; R = C$_6$H$_5$
DM-SEGPHOS; R = 3,5-(CH$_3$)$_2$C$_6$H$_3$
DTBM-SEGPHOS; R = 4-CH$_3$O-3,5-(t-C$_4$H$_9$)$_2$C$_6$H$_2$

FIG. A: Optically active SEGPHOS derivative

[Chem. 12]

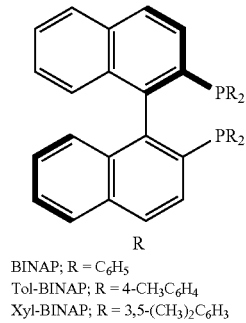

BINAP; R = C$_6$H$_5$
Tol-BINAP; R = 4-CH$_3$C$_6$H$_4$
Xyl-BINAP; R = 3,5-(CH$_3$)$_2$C$_6$H$_3$

FIG. B: Optically active BINAP derivative

[Chem. 13]

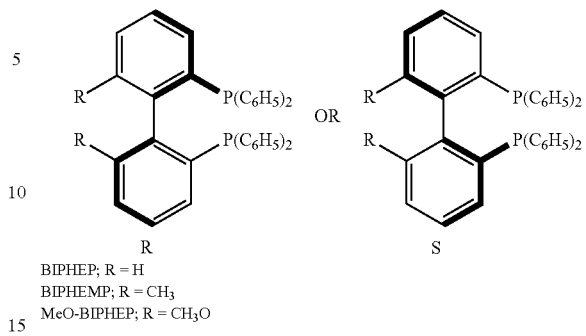

BIPHEP; R = H
BIPHEMP; R = CH$_3$
MeO-BIPHEP; R = CH$_3$O

FIG. C: Optically active BIPHEP derivative

[Chem. 14]

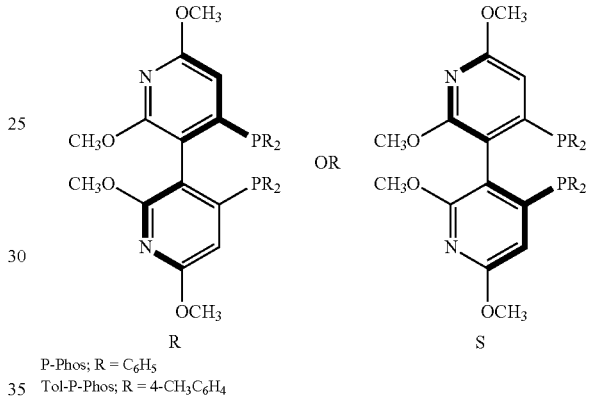

P-Phos; R = C$_6$H$_5$
Tol-P-Phos; R = 4-CH$_3$C$_6$H$_4$
Xyl-P-Phos; R = 3,5-(CH$_3$)$_2$C$_6$H$_3$ FIG. D: Optically active P-Phos derivative

[Chem. 15]

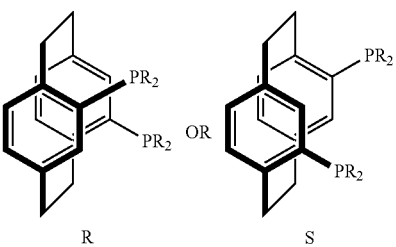

PhanePhos; R = C$_6$H$_5$
Tol-PhanePhos; R = 4-CH$_3$C$_6$H$_4$
Xyl-PhanePhos; R = 3,5-(CH$_3$)$_2$C$_6$H$_3$ FIG. E: Optically active PhanePhos derivative

[Chem. 16]

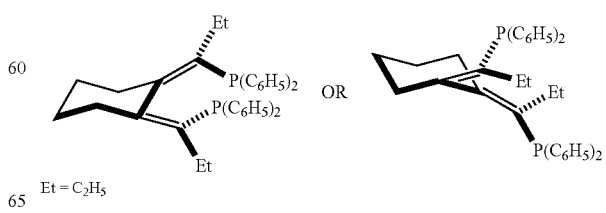

Et = C$_2$H$_5$

FIG. F: Optically active 1,4-Et$_2$-cyclo-C$_6$H$_8$-NUPHOS

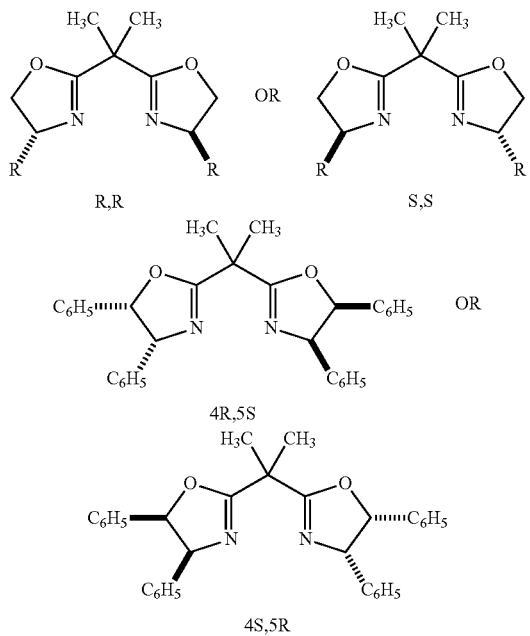

R = i-C₃H₇
R = t-C₄H₉
R = C₆H₅

FIG. G: Optically active BOX derivative

Other example of the transition metal complex with the optically active ligand are BINOL-Ti complexes as represented by the general formula [8]

[Chem. 18]

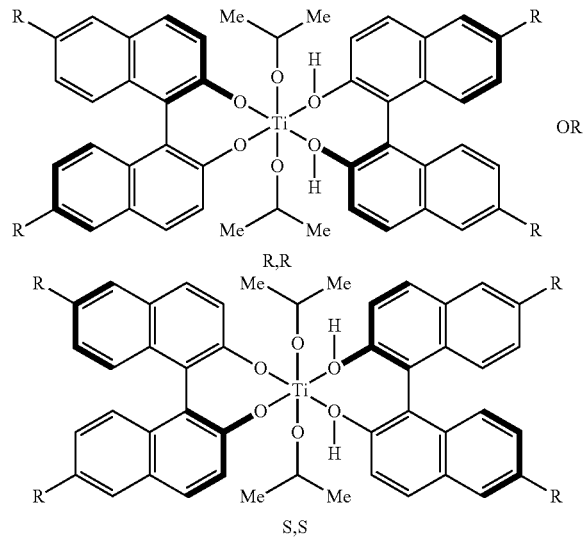

where R represents a hydrogen atom, a chlorine atom, a bromine atom, an iodine atom or a trifluoromethyl group; and Me represents a methyl group.

Among others, it is preferable to use a divalent cationic transition metal complex with an optically active ligand, more preferably a divalent cationic palladium complex with an optically active ligand. (Although typical examples of the optically active ligand are mentioned above, there can suitably be used as the optically active ligand any appropriate one of those described in "Catalytic Asymmetric Synthesis", Second Edition, 2000, Wiley-VCH, Inc. As Z, $SbF_6$, $BF_4$, OTf and $B(3,5-(CF_3)_2C_6H_3)_4$ are preferred. Particularly preferred are $SbF_6$, OTf and $B(3,5-(CF_3)_2C_6H_3)_4$.)

These complexes can be prepared by any known process (see e.g. Tetrahedron Letters (U.K.), 2004, Vol. 45, P. 183-185; Tetrahedron: Asymmetry (U.K.), 2004, Vol. 15, P. 3885-3889; Angew. Chem. Int. Ed. (Germany), 2005, Vol. 44, P. 7257-7260; J. Org. Chem. (U.S.), 2006, Vol. 71, P. 9751-9764; J. Am. Chem. Soc. (U.S.), 1999, Vol. 121, P. 686-699; Nature (U.K.), 1997, Vol. 385, P. 613-615). The complex can be provided in isolate form or can be prepared in advance in the reaction system and used without isolation. Further, the complex may be in the form of having a coordinate bond (solvation) with water or organic solvent such as acetonitrile.

There may be used, in the same manner as the divalent cationic transition metal complex with the optically active ligand as represented by the general formula [7], a cationic binuclear transition metal complex with an optically active ligand as represented by the general formula [9]

[Chem. 19]

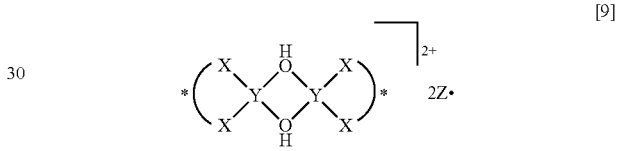

where X—*—X, Y and Z are the same as in the general formula [7].

The configuration ((R), (S), (R,R), (S,S) etc.) of the optically active ligand can be selected as appropriate depending on the configuration of the target optically active fluorinated oxetane. The optical purity of the optically active ligand can also be set as appropriate depending on the optical purity of the target optically active fluorinated oxetane. In general, it suffices that the optical purity (enantiomer excess) of the optically active ligand is 95% ee or higher. The optical purity (enantiomer excess) of the optically active ligand is preferably 97% ee, more preferably 99% ee. Among the above optically active ligands, the BINAP derivative is suitably used for the reason that the BINAP derivative can be most cheaply available in the form of both enantiomers and, when derived into an asymmetric catalyst, attain very high activity. As the BINAP derivative, BINAP and Tol-BINAP are preferred. Particularly preferred is BINAP.

It suffices to use the transition metal complex with the optically active ligand in an amount of 0.4 mol or less per 1 mol of the acyl alkenyl ether of the general formula [2]. The amount of the transition metal complex with the optically active ligand used is preferably 0.3 to 0.00001 mol, more preferably 0.2 to 0.0001 mol, per 1 mol of the acyl alkenyl ether of the general formula [2].

Examples of the reaction solvent are: aliphatic hydrocarbon solvents such as n-pentane, n-hexane, cyclohexane and n-heptane; aromatic hydrocarbon solvents such as benzene, toluene, xylene and mesitylene; halogenated hydrocarbon solvents such as methylene chloride, chloroform and 1,2-dichloroethane; and ether solvents such as diethyl ether, tert-butyl methyl ether and 1,4-dioxane. Among others, aromatic hydrocarbon solvents, halogenated hydrocarbon solvents and ether solvents are preferred. Particularly preferred are aromatic hydrocarbon solvents and halogenated hydrocarbon solvents. These reaction solvents can be used solely or in combination thereof. In the production method of the present invention, the reaction can be performed in the absence of the reaction solvent (i.e. under neat conditions). This is one preferred embodiment of the present invention as it is possible to dramatically reduce the amount of use of the transition metal complex with the optically active ligand.

In the case of using the reaction solvent, there is no particular limitation on the amount of the reaction solvent used. It suffices to use the reaction solvent in an amount of 0.01 L or more per 1 mol of the acyl alkenyl ether of the general formula [2]. The amount of the reaction solvent used is preferably 0.05 to 50 L, more preferably 0.1 to 30 L, per 1 mol of the acyl alkenyl ether of the general formula [2]. In the production method of the present invention, the reaction can be performed at a high concentration of substrate (i.e. with the use of a small amount of reaction solvent). This is also one preferred embodiment of the present invention as it is possible to dramatically reduce the amount of use of the transition metal complex with the optically active ligand. For such a substrate concentration, it suffices to use the reaction solvent in an amount of less than 1 L per 1 mol of the acyl alkenyl ether of the general formula [2]. The amount of the reaction solvent used is preferably 0.5 L or less, more preferably 0.3 L or less, per 1 mol of the acyl alkenyl ether of the general formula [2].

It suffices that the reaction temperature is in a range of −80 to +150° C. The reaction temperature is preferably −70 to +125° C., more preferably −60 to +100° C.

Further, it suffices that the reaction time is in a range of 72 hours or less. As the reaction time depends on the raw material substrate, the asymmetric catalyst and the reaction conditions, it is preferable to determine the time at which the raw material substrate has almost disappeared as the end of the reaction while monitoring the progress of the reaction by any analytical means such as gas chromatography, thin layer chromatography, liquid chromatography or nuclear magnetic resonance (NMR).

The target optically active fluorinated oxetane of the general formula [3] is obtained by post treatment of the reaction terminated liquid. The post treatment can be performed by ordinary operation in organic synthesis. The obtained crude product can be purified to a high purity, as required, by purification operation such as activated carbon treatment, distillation, recrystallization or column chromatography. The asymmetric catalyst used in the present invention is one kind of Lewis acid. Even in the case where the target product is unstable toward acids, it is possible to effectively prevent decomposition of the target product and occurrences of side reactions by performing the reaction under low-temperature conditions and directly adding an organic base (catalyst poison) such as triethylamine to the reaction terminated liquid. The high-purity product can be obtained by relatively easy operation of directly passing the mixed solution of the reaction terminated liquid and the organic base (as the treated reaction solution) through a short column, concentrating the filtrate and purifying the concentration residue by column chromatography.

When $R^4$ or $R^5$ is a hydrogen atom in the acyl alkenyl ether of the general formula [2], the optically active fluorinated oxetane product of the general formula [3] may undergo ring-opening reaction and thereby be obtained in a ring-open form of the general formula [10]

[Chem. 20]

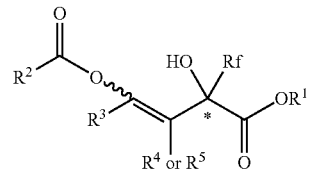

[10]

where Rf represents a perfluoroalkyl group; $R^1$ represents an alkyl group; $R^2$, $R^3$, $R^4$ and $R^5$ each independently represent a hydrogen atom, an alkyl group, a substituted alkyl group, an aromatic ring group or a substituted aromatic ring group; * represents an asymmetric carbon atom; and the wavy lines indicate that the double bond is in either or both of E and Z geometries.

The optically active fluorinated oxetane of the general formula [3] as claimed in the present invention is thus defined as including the optically active fluorinated oxetane ring-open product of the general formula [10].

EXAMPLES

The present invention will be described in more detail below by way of the following examples. It should be noted that these examples are illustrative and are not intended to limit the present invention thereto.

Herein, Examples 2 to 8 were performed in the same manner as in Example 1. The results of Examples 1 to 9 are summarized in TABLE 1. The substrate concentration were 2 M, 1 M and 0.5 M when the amount of the reaction solvent used was 0.5 L, 1 L and 2 L with reference to 1 mol of the raw material substrate, respectively.

Example 1

To 1.0 mL of toluene, 8.0 mg (0.01 mmol) of (R)-BINAP-PdCl$_2$ represented by the following formula:

[Chem. 21]

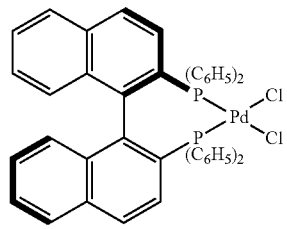

and 7.6 mg (0.022 mmol) of AgSbF$_6$ were added in a nitrogen atmosphere. The resulting solution was stirred for 30 minutes at room temperature (to thereby form a divalent cationic transition metal complex with an optically active ligand as represented by the general formula [7] (X—*—X: (R)-BINAP, Y: Pd, Z: SbF$_6$) in the reaction system).

To the solution, 34.0 mg (0.2 mmol) of fluorinated α-keto ester of the following formula:

[Chem. 22]

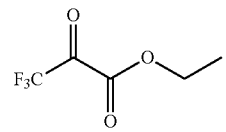

and 8.6 mg (0.1 mmol) of acyl alkenyl ether of the following formula:

[Chem. 23]

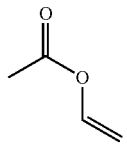

were added at −20° C. The solution was then stirred for 15 hours as the same temperature (as a reaction terminated liquid) and treated with the addition of 218 mg (2.2 mmol) of triethylamine.

The treated reaction solution was directly passed through a short column (silica gel/ethyl acetate:n-hexane=1:1). The filtrate was concentrated under a reduced pressure. The concentration residue was subjected to $^1$H-NMR quantitative analysis. It was confirmed that there was contained in the residue 22.8 mg of (+)-isomer of optically active fluorinated oxetane of the following formula:

[Chem. 24]

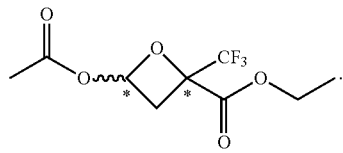

The yield was 89%. The diastereoisomer ratio was determined by $^1$H-NMR to be 23/77. Further, the enantiomer excess were determined by chiral gas chromatography (CP-Chirasil-Dex CB) to be 91% ee and 98% ee, respectively. The $^1$H-, $^{13}$C- and $^{19}$F-NMR data are indicated below.

$^1$H-NMR [300.1 MHz, CDCl$_3$, (CH$_3$)$_4$Si] δ; 1.33 (t, J=7.2 Hz, 3H), 2.12 (s, 3H), 3.04 (ddd, J=0.3 Hz, 4.2 Hz, 13.2 Hz, 2H), 3.27 (dd, J=5.4 Hz, 13.2 Hz, 2H), 4.35 (q, J=7.2 Hz, 2H), 6.48 (dd, J=5.4 Hz, 4.2 Hz, 1H).

$^{13}$C-NMR [75.5 MHz, CDCl$_3$, (CH$_3$)$_4$Si] δ; 13.7, 20.6, 33.5, 62.9, 78.2 (q, J$_{C-F}$=34.0 Hz), 93.5, 122.8 (q, J$_{C-F}$=283.1 Hz), 165.5, 168.8.

$^{19}$F-NMR [282.4 MHz, CDCl$_3$, C$_6$H$_5$CF$_3$] δ; −79.5.

Example 9

To 1.70 g (10 mmol) of fluorinated α-keto ester of the following formula:

[Chem. 25]

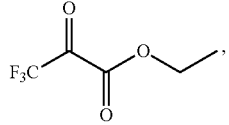

4.0 mg (0.005 mmol) of (R)-BINAP-PdCl$_2$ represented by the following formula:

[Chem. 26]

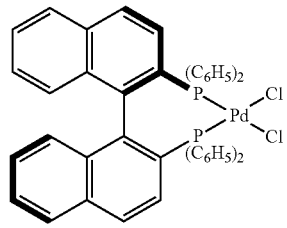

and 3.8 mg (0.011 mmol) of AgSbF$_6$ were added in a nitrogen atmosphere. The resulting solution was stirred for 30 minutes at room temperature (to thereby form a divalent cationic transition metal complex with an optically active ligand as represented by the general formula [7] (X—*—X: (R)-BI-NAP, Y: Pd, Z: SbF$_6$) or a complex of the divalent cationic transition metal complex with the optically active ligand and the fluorinated α-keto ester as represented by the following formula:

[Chem. 27]

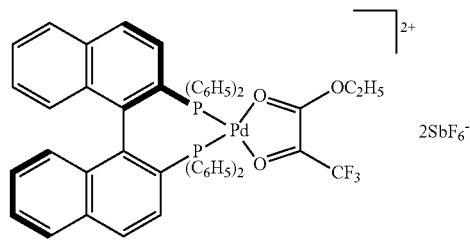

in the reaction system).

To the solution, 430 mg (5 mmol) of acyl alkenyl ether of the following formula:

[Chem. 28]

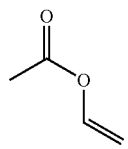

was added at −20° C. The solution was then stirred for 48 hours as the same temperature (as a reaction terminated liquid) and treated with the addition of 218 mg (2.2 mmol) of triethylamine.

The treated reaction solution was directly passed through a short column (silica gel/ethyl acetate:n-hexane=1:1). The filtrate was concentrated under a reduced pressure. The concentration residue was purified by column chromatography (silica gel/ethyl acetate:n-hexane=1:4). With this, there was obtained 1.10 g of (+)-isomer of optically active fluorinated oxetane of the following formula:

[Chem. 29]

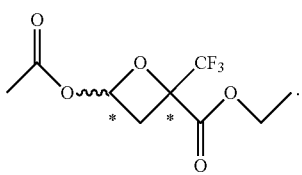

The yield was 86%. The diastereoisomer ratio was determined by $^1$H-NMR to be 8/92. The enantiomer excess were determined by chiral gas chromatography (CP-Chirasil-Dex CB) to be 20% ee and 96% ee, respectively. The specific rotation was $[\alpha]_D^{24}$+48.86 (c=1.13 in CHCl$_3$). The $^1$H-, $^{13}$C- and $^{19}$F-NMR data were the same as those of Example 1.

Example 10

To 5.00 g (29.4 mmol) of fluorinated α-keto ester of the following formula:

[Chem. 30]

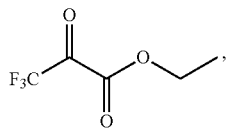

120 mg (0.150 mmol) of (S)-BINAP-PdCl$_2$ represented by the following formula:

TABLE 1

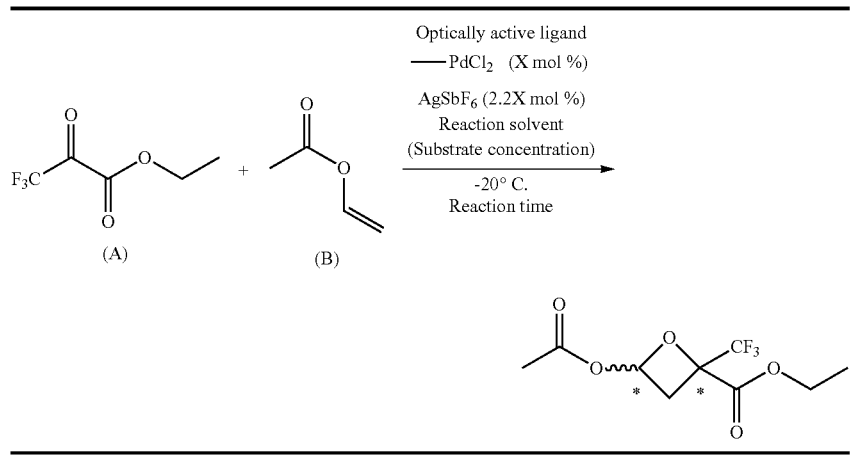

| Example | Optically active ligand | X mol % [a] | Amount of A used | Amount of B used | Reaction solvent (substrate concentration) [b] |
|---------|------------------------|-------------|------------------|------------------|------------------------------------------------|
| 1 | (R)-BINAP | 10 mol % | 0.2 mmol | 0.1 mmol | toluene (0.1M) |
| 2 | (R)-Tol-BINAP | 10 mol % | 0.2 mmol | 0.1 mmol | toluene (0.1M) |
| 3 | (R)-SEGPHOS | 10 mol % | 0.2 mmol | 0.1 mmol | toluene (0.1M) |
| 4 | (R)-BINAP | 10 mol % | 0.2 mmol | 0.1 mmol | methylene chloride (0.1M) |
| 5 | (R)-BINAP | 5 mol % | 0.2 mmol | 0.1 mmol | toluene (0.1M) |
| 6 | (R)-BINAP | 5 mol % | 0.1 mmol | 0.1 mmol | toluene (0.1M) |
| 7 | (R)-BINAP | 5 mol % [f] | 0.1 mmol | 0.2 mmol | toluene (0.1M) [g] |
| 8 | (R)-BINAP | 0.1 mol % | 10 mmol | 5 mmol | toluene (5M) |
| 9 | (R)-BINAP | 0.1 mol % | 10 mmol | 5 mmol | no reaction solvent (neat condition) |

| Example | Reaction time | Yield [c] | Diastereoisomer ratio [d] | Enantiomer excess [e] |
|---------|---------------|-----------|---------------------------|-----------------------|
| 1 | 15 hr | 89% | 23/77 | 91% ee/98% ee |
| 2 | 15 hr | 85% | 22/78 | 90% ee/98% ee |
| 3 | 15 hr | 47% | 24/76 | 83% ee/93% ee |
| 4 | 15 hr | 78% | 35/65 | 94% ee/98% ee |
| 5 | 24 hr | 89% | 20/80 | 89% ee/96% ee |
| 6 | 24 hr | 59% | 22/78 | 84% ee/97% ee |
| 7 | 24 hr | 52% [h] | 13/87 | 78% ee/97% ee |
| 8 | 48 hr | 61% [i] | 9/91 | 56% ee/96% ee |
| 9 | 48 hr | 86% [i] | 8/92 | 20% ee/96% ee |

[a] Mol % relative to B.
[b] Substrate concentration relative to B.
[c] $^1$H-NMR yield relative to B.
[d] Determined by $^1$H-NMR.
[e] Determined by chiral gas chromatography (CP-Chirasil-Dex CB).
[f] Mol % relative to A.
[g] Substrate concentration relative to A.
[h] $^1$H-NMR yield relative to A.
[i] Isolation yield.

[Chem. 31]

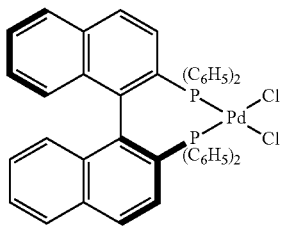

and 113 mg (0.329 mmol) of AgSbF$_6$ were added in a nitrogen atmosphere. The resulting solution was stirred for 30 minutes at room temperature (to thereby form a divalent cationic transition metal catalyst with an optically active ligand as represented by the general formula [7] (X—*—X: (S)-BINAP, Y: Pd, Z: SbF$_6$) or a complex of the divalent cationic transition metal complex with the optically active ligand and the fluorinated α-keto ester as represented by the following formula:

[Chem. 32]

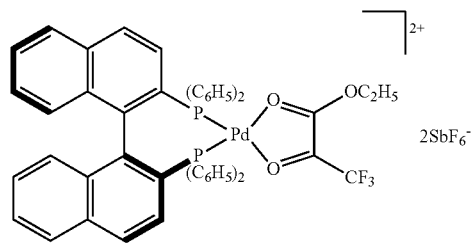

in the reaction system).

To the solution, 46.0 g (270 mmol) of fluorinated α-keto ester of the following formula:

[Chem. 33]

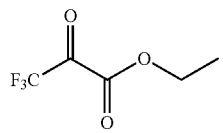

and 12.9 g (150 mmol) of acyl alkenyl ether of the following formula:

[Chem. 34]

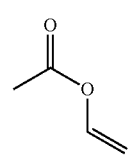

were added at −20° C. The solution was then stirred for 48 hours as the same temperature (as a reaction terminated liquid) and treated with the addition of 6.68 g (66.0 mmol) of triethylamine.

The treated reaction solution was directly passed through a short column (silica gel/ethyl acetate:n-hexane=1:1). The filtrate was concentrated under a reduced pressure. The concentration residue was subjected to $^{19}$F-NMR quantitative analysis. It was confirmed that there was contained in the residue 20.3 g of (−)-isomer of optically active fluorinated oxetane of the following formula:

[Chem. 35]

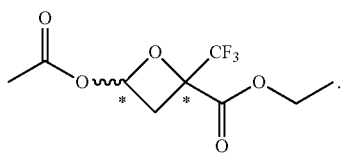

The yield was 53%. The crude product was purified by fractional distillation (boiling point: 106° C./vacuum degree: 0.7 kPa), thereby yielding 17.3 g of a main fraction. The recovery rate was 85% (the total yield was 45%). The diastereoisomer ratio of the main fraction was determined by gas chromatography to be 4/96. Further, the enantiomer excess of the main diastereomer was determined by chiral gas chromatography (CP-Chirasil-Dex CB) to be 98% ee. The $^1$H- and $^{19}$F-NMR data were the same as those of Example 1.

Example 11

To 5.00 g (29.4 mmol) of fluorinated α-keto ester of the following formula:

[Chem. 36]

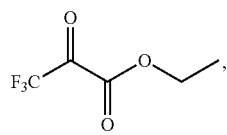

120 mg (0.150 mmol) of (S)-BINAP-PdCl$_2$ represented by the following formula:

[Chem. 37]

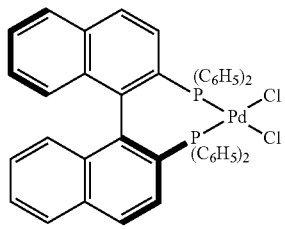

and 113 mg (0.329 mmol) of AgSbF$_6$ were added in a nitrogen atmosphere. The resulting solution was stirred for 30 minutes at room temperature (to thereby form a divalent cationic transition metal complex with an optically active ligand as represented by the general formula [7] (X—*—X: (S)-BINAP, Y: Pd, Z: SbF$_6$) or a complex of the divalent cationic transition metal complex with the optically active ligand and the fluorinated α-keto ester as represented by the following formula:

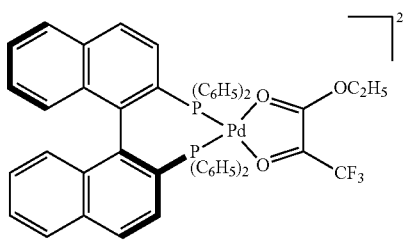

in the reaction system).

To the solution, 46.0 g (270 mmol) of fluorinated α-keto ester of the following formula:

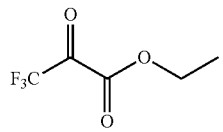

and 15.0 g (150 mmol) of acyl alkenyl ether of the following formula:

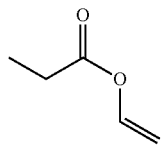

were added at −20° C. The solution was then stirred for 48 hours as the same temperature (as a reaction terminated liquid) and treated with the addition of 6.68 g (66.0 mmol) of triethylamine.

The treated reaction solution was directly passed through a short column (silica gel/ethyl acetate:n-hexane=1:1). The filtrate was concentrated under a reduced pressure. The concentration residue was subjected to $^{19}$F-NMR quantitative analysis. It was confirmed that there was contained in the residue 22.0 g of (−)-isomer of optically active fluorinated oxetane of the following formula:

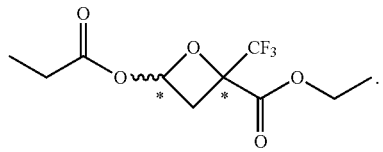

The yield was 54%. The crude product was purified by fractional distillation, thereby yielding 18.6 g of a main fraction. The recovery rate was 85% (the total yield was 46%). The diastereoisomer ratio of the main fraction was determined by gas chromatography to be 4/96. Further, the enantiomer excess of the main diastereomer was determined by chiral gas chromatography (CP-Chirasil-Dex CB) to be 97% ee. The $^1$H- and $^{19}$F-NMR data are indicated below.

$^1$H-NMR [reference material: $(CH_3)_4Si$, deuterium solvent: $CDCl_3$] δ ppm/1.16 (t, 3H), 1.35 (t, 3H), 2.42 (m, 2H), 3.08 (m, 1H), 3.29 (m, 1H), 4.38 (q, 2H), 6.52 (m, 1H).

$^{19}$F-NMR [reference material: $C_6F_6$, deuterium solvent: $CDCl_3$] δ ppm/+82.33 (s, 3F).

The invention claimed is:

1. A method for producing an optically active fluorinated oxetane of the general formula [3], comprising:
    reacting a fluorinated α-keto ester of the general formula [1] with an acyl alkenyl ether of the general formula [2] in the presence of a transition metal complex with an optically active ligand,
    wherein the transition metal complex with the optically active ligand is present in an amount less than a stoichiometric amount,

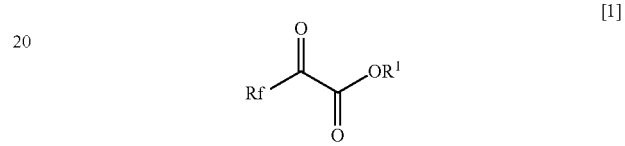

where Rf represents a perfluoroalkyl group; and $R^1$ represents an alkyl group;

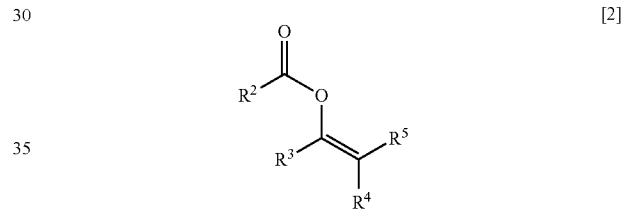

where $R^2$, $R^3$, $R^4$ and $R^5$ each independently represent a hydrogen atom, an alkyl group, a substituted alkyl group, an aromatic ring group or a substituted aromatic ring group; and

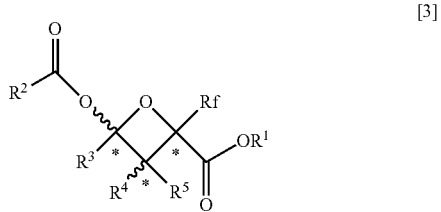

where Rf, $R^1$, $R^2$, $R^3$, $R^4$ and $R^5$ are the same as above: * represents an asymmetric carbon atom (when $R^4$ and $R^5$ are the same substituents, a carbon atom to which $R^4$ and $R^5$ are bonded is not an asymmetric carbon atom); and the wavy lines indicate that the configuration of acyloxy ($R^2CO_2$) group relative to Rf and the configuration of $R^4$ relative to Rf are each independently a syn configuration, an anti configuration or a mixture thereof.

2. The method according to claim 1, wherein the optically active. fluorinated oxetane is of the general formula [6]; wherein the fluorinated α-keto ester is of the general formula [4]; wherein the acyl alkenyl ether is of the general formula [5]; and wherein the transition metal complex with the optically active ligand is a divalent cationic transition metal complex with an optically active ligand,

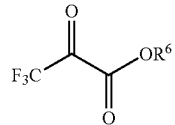

[4]

where $R^6$ represents a methyl group or an ethyl group;

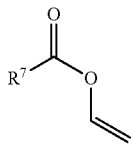

[5]

where $R^7$ represents a hydrogen atom or an alkyl group; and

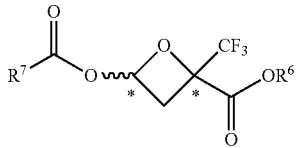

[6]

where $R^6$ and $R^7$ are the same as above; * represents an asymmetric carbon atom; and the wavy line indicates that the configuration of acyloxy ($R^7CO_2$) group relative to $CF_3$ group is a syn configuration, an anti configuration or a mixture thereof.

3. The method according to claim 2, wherein the divalent cationic transition metal complex with the optically active ligand is a divalent cationic palladium complex with an optically active ligand.

4. An optically active fluorinated oxetane of the general formula [3]

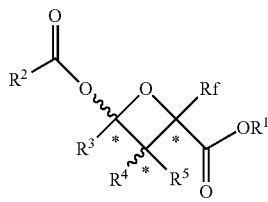

[3]

where Rf represents a perfluoroalkyl group; $R^1$ represents an alkyl group; $R^2$, $R^3$, $R^4$ and $R^5$ each independently represent a hydrogen atom, an alkyl group, a substituted alkyl group, an aromatic ring group or a substituted aromatic ring group; * represents an asymmetric carbon atom (when $R^4$ and $R^5$ are the same substituents, a carbon atom to which $R^4$ and $R^5$ are bonded is not an asymmetric carbon atom); and the wavy lines indicate that the configuration of acyloxy ($R^2CO_2$) group relative to Rf and the configuration of $R^4$ relative to Rf are each independently a syn configuration, an anti configuration or a mixture thereof.

5. The optically active fluorinated oxetane according to claim 4, wherein the optically active fluorinated oxetane is of the general formula [6]

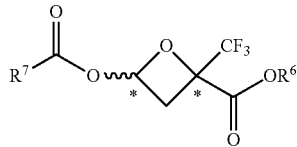

[6]

where $R^6$ represents a methyl group or an ethyl group; $R^7$ represents a hydrogen atom or an alkyl group; * represents an asymmetric carbon atom; and the wavy line indicates that the configuration of acyloxy ($R^7CO_2$) group relative to $CF_3$ group is a syn configuration, an anti configuration or a mixture thereof relative to $CF_3$ group.

\* \* \* \* \*